United States Patent
Segal

(10) Patent No.: US 9,265,892 B2
(45) Date of Patent: Feb. 23, 2016

(54) MEDICAMENT DISPENSING DEVICE

(71) Applicant: Eric Segal, North York (CA)

(72) Inventor: Eric Segal, North York (CA)

(73) Assignee: Eric Segal (CA)

( * ) Notice: Subject to any disclaimer, the term of this patent is extended or adjusted under 35 U.S.C. 154(b) by 0 days.

(21) Appl. No.: 14/168,644

(22) Filed: Jan. 30, 2014

(65) Prior Publication Data

US 2014/0207102 A1 Jul. 24, 2014

Related U.S. Application Data

(63) Continuation-in-part of application No. 13/319,216, filed as application No. PCT/CA2010/000694 on May 7, 2010, now Pat. No. 8,708,971.

(60) Provisional application No. 61/176,128, filed on May 7, 2009.

(51) Int. Cl.
| | |
|---|---|
| *A61M 31/00* | (2006.01) |
| *A61M 5/315* | (2006.01) |
| *A61M 5/20* | (2006.01) |
| *A61M 5/32* | (2006.01) |
| *A61M 5/50* | (2006.01) |

(52) U.S. Cl.
CPC ............ *A61M 5/3158* (2013.01); *A61M 5/2033* (2013.01); *A61M 5/3157* (2013.01); *A61M 5/31591* (2013.01); *A61M 5/326* (2013.01); *A61M 5/5086* (2013.01); *A61M 2005/3152* (2013.01); *A61M 2005/3247* (2013.01); *A61M 2005/3267* (2013.01); *A61M 2205/586* (2013.01)

(58) Field of Classification Search
CPC ................... A61M 2005/2033; A61M 5/3202; A61M 2005/2086; A61M 5/3158; A61M 5/24; A61M 5/00; A61M 2005/2013; A61M 2005/202; A61M 2005/2026; A61M 2005/2073; A61M 2005/208; A61M 5/315; A61M 5/31; A51M 5/20
USPC .......................................................... 604/110
See application file for complete search history.

(56) References Cited

U.S. PATENT DOCUMENTS

| | | | |
|---|---|---|---|
| 5,378,233 A * | 1/1995 | Haber | A61M 5/19 604/135 |
| 6,241,709 B1 | 6/2001 | Bechtold et al. | |
| 6,607,508 B2 * | 8/2003 | Knauer | 604/131 |
| 6,689,108 B2 | 2/2004 | Lavi et al. | |

FOREIGN PATENT DOCUMENTS

| | | |
|---|---|---|
| EP | 1932558 | 6/2008 |
| GB | 2396298 A | 6/2004 |
| WO | 2005009515 | 2/2005 |

* cited by examiner

*Primary Examiner* — Nathan R Price
*Assistant Examiner* — Morgan Lee

(57) ABSTRACT

A portable medicament dispensing device having a mechanism which is not susceptible to jamming for dispensing the medication to a user. The device employs employs a coupling for coupling the relative motion between reciprocating body members housing the ancillary components and a barrel plunger associated with the syringe. One embodiment provides a pivoting coupling whereas an alternate uses a rack and pinion system. The advantage of simplifying such mechanisms results in a structure which has smooth unemcumbered motion with fewer parts to avoid mechanical jamming during use.

16 Claims, 10 Drawing Sheets

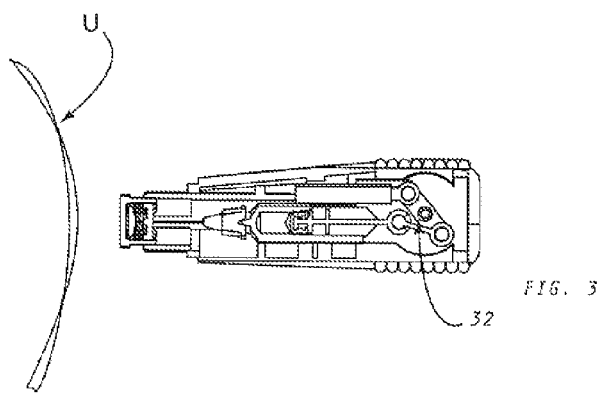
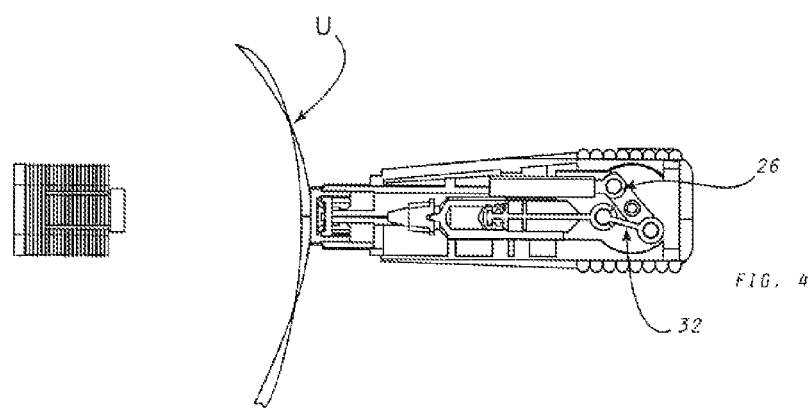
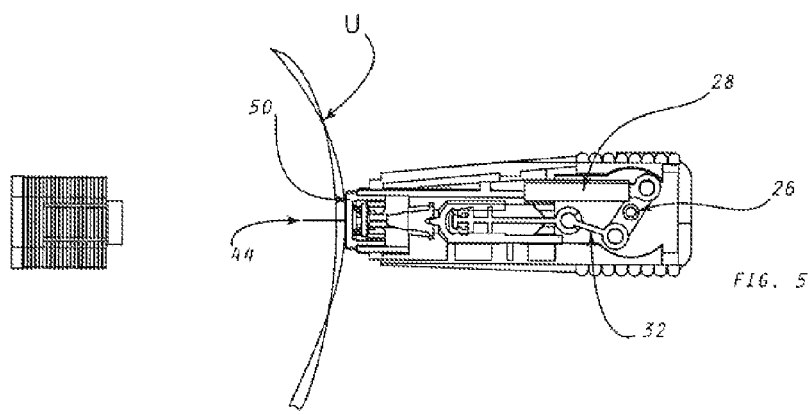
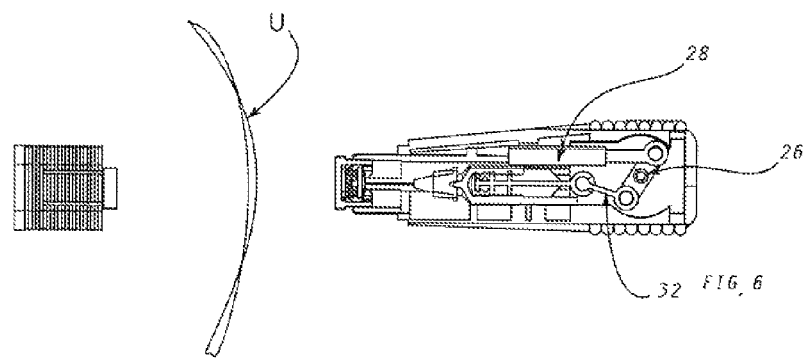

MEDICAMENT DISPENSING DEVICE

REFERENCE TO RELATED APPLICATIONS

This application is a continuation in part of U.S. patent application Ser. No. 13/319,216 filed Nov. 7, 2011, which issued as U.S. Pat. No. 8,708,971 on Apr. 29, 2014, which claims priority to International Application No. PCT/CA2012/00694 filed May 7, 2010, and U.S. Provisional Application No. 61/176,128 filed May 7, 2009.

FIELD OF THE INVENTION

The present invention relates to a medicament dispenser and more particularly, the present invention relates to a structure for dispensing a medicament where the structure has a mechanical coupling member to substantially reduce jamming of the components normally attributable to such devices.

BACKGROUND OF THE INVENTION

Single use single dose medicament delivery devices are widely known and are generally used to dispense medicaments such as epinephrine in an urgent manner to a user, the so called "epi pen" is a typical example of such arrangements. One of the significant disadvantages inherent with these devices relates to jamming. The existing devices often employ spring configurations for movement of key parts such as the needle as well as the barrel which assists in delivery of the medicament to the needle. in the scenario where a jam has occurred, the result can he fatal if the user cannot repair the device to function properly. in some instances, repair is impossible given urgent time constraints and the user is forced to dismantle or destroy the structure in order to gain access to the medication.

The above is possible where the user is not a child or a user otherwise not capable of achieving access. To address the limitations in the art, a variety of solutions have been advanced in the art. An example is provided in U.S. Pat. No. 6,808,507, issued Oct. 26, 2004, to Roser. In the arrangement discussed in this patent, a telescopic member is provided and a spring surrounds the needle. The arrangement is useful, however, there is still a possibility that the spring could be defective or otherwise fail, thus complicating delivery.

Botich et al., in U.S. Pat. No. 6,039,713, issued Mar. 21, 2000, teach a pre-filled retractable needle device. The device, as is common with most arrangements, includes reciprocating body members, springs, etc. in this instance the device has a number of movable parts which elevates the possibility for jamming or failure.

U.S. Pat. No. 6,846,301, issued to Smith et al., Jun. 25, 2005, teaches a disposable safety syringe with a vacuum system to withdraw the needle into the body after use. There is no provision for a mechanical linkage for quick delivery of the medicament.

Given the extent of development in the prior art, there exists a need for an improved medicament dispenser which is efficient and reliable while maintaining a lower profile than those devices currently available.

The present invention provides a significantly improved arrangement which is devoid of the structural limitations inherent with the prior art.

SUMMARY OF THE INVENTION

One object of one embodiment of the present invention is to provide an improved medicament dispensing device.

A further object of one embodiment of the present invention is to provide an automatic injection device for dispensing a medicament, said device having a needle connected to a barrel adapted to retain medicament and a plunger within said barrel. The device comprises an outside first body member and a second body member coaxially mounted for reciprocal movement within said outside first body member, said outside body member housing said needle, said barrel and said plunger; a first rack and a second rack housed within said outside first body member; a third rack connected to said plunger; and pinion means mounted within said outside first body member and between said first rack and said third rack and between said second rack and said third rack, said second body member including a needle cover biased to cover said needle and movable to expose said needle in use and to move said first rack and said second rack for urging said plunger into said barrel to dispense said medicament.

Another object of one embodiment of the present invention is to provide a method for dispensing a medicament from a device having a needle, connected to a barrel adapted to retain medicament and a plunger within the barrel, said device having a first body member and a second body member mounted thereon for reciprocal movement comprising the steps of providing a cover means for covering a tip of the needle; positioning the device in contact adjacent a user's skin; urging the device against the user to expose, in a first stage, the needle through the cover means; continuing to move the cover means to activate reciprocal movement of the plunger where the needle penetrates a user's skin and the medicament is forced by the plunger movement through said barrel and the needle to deliver the medicament to the user.

Having thus generally described the invention, reference will now be made to the accompanying drawings, illustrating preferred embodiments.

BRIEF DESCRIPTION OF THE DRAWINGS

FIGS. 3 through 6 are cross sections of the device sequentially illustrating the components positions as the device is advance through a pre-use position through to use and withdrawal;

Similar numerals used in the drawings denote similar elements.

DETAILED DESCRIPTION OF THE PREFERRED EMBODIMENTS

Figure 1:
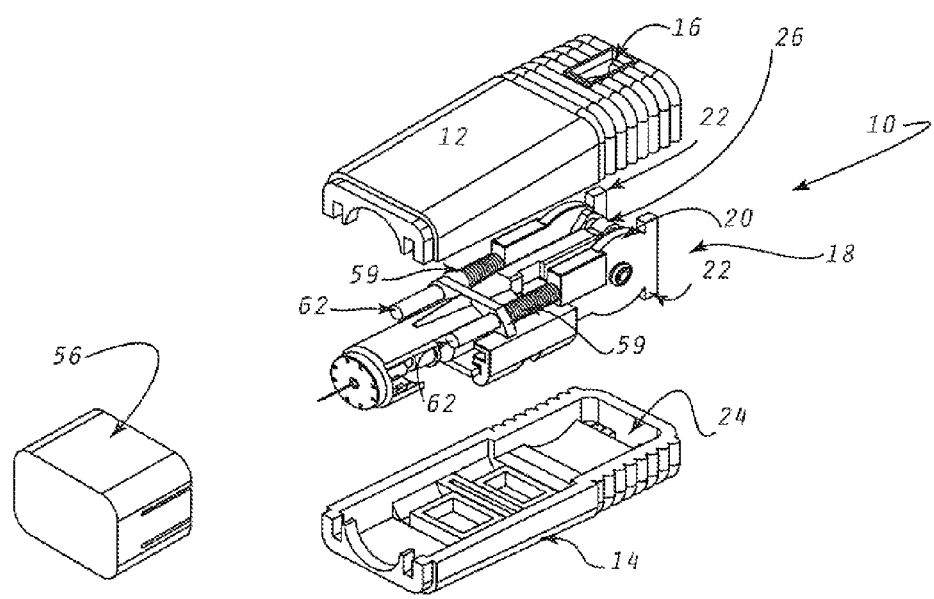
FIG. 1 is an exploded view of the arrangement according to one embodiment of the present invention.

Referring now to the drawings, FIG. 1 illustrates one embodiment of the present invention. The overall arrangement is denoted by numeral 10. The arrangement provides an exterior body, shown in the example in two sections 12 and 14. Section 12 provides an opening 16 to allow a user visibility of the interior to determine that the device has been discharged. This will be discussed in greater detail herein after.

Turning to the major components of the device, a second body member 18 is configured for reception and slidable movement with the exterior body supra. Member 18 has a mounting 20 with, as shown in the example, projections 22 configured for fixed location in seating 24 in body members 12 and 14. A drive member 26 is rotatably connected to mounting 20 and at one end thereof has a pivotally connected use indicator member 28 at pivot point 30 for indicating when the unit is used. The opposed end of member 26 pivotally connects coupling member 32 at pivot point 30. Member 32, at the opposed end thereof, has a pivotal connection 36. The connection at 36 is with a barrel plunger 38 received within barrel 40. Barrel 40 terminates in needle hilt 42 which, in turn, receives needle 44. As is illustrated, the barrel 40 retains a predetermined amount of medicament forwardly of plunger 38.

In order to provide protection and sterility to the device 10, the same includes a cover 50. The same is configured to always extend outwardly sufficiently to completely cover the tip of the needle. In this manner, springs 48 or other resilient means urge cover member 50 outwardly of a terminal end 52 of body 18. The cover member 50 also provides a foam cap 54 or other resilient material which protects the tip of the needle 44. This also assists in preventing spillage from the tip. As a further precaution and for adding durability and aesthetic appeal, a secondary cap 56 is frictionally retained by body members 12 and 14 at perimeter lip 58.

Figure 2:
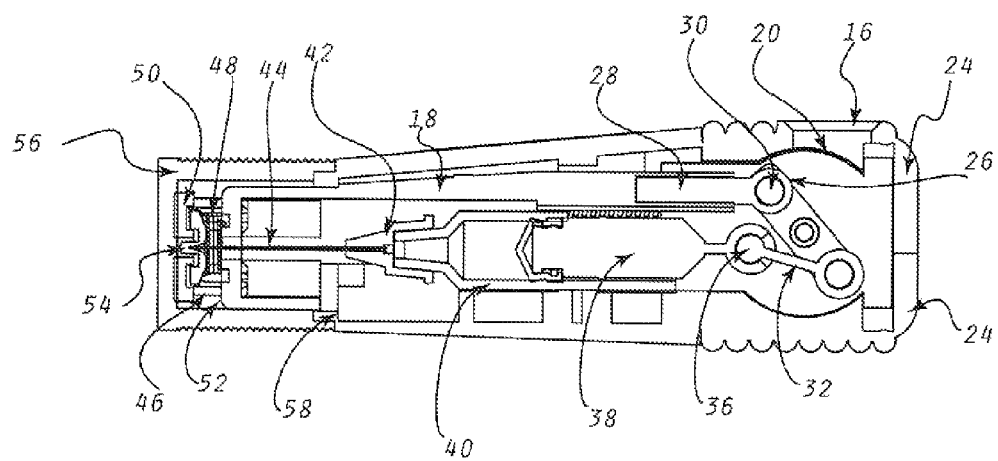
FIG. 2 is a cross section of FIG. 1 with the arrangement shown in the ready to use state.

In order to bias the needle 44 in the position shown in FIG. 2, the storage or standby position, springs 59 are provided extending between mount 20 and spring retainers 62. FIG. 1 illustrates the springs in a compressed state.

With reference to FIGS. 3 through 6, shown are the various dispositions of the elements from a pre-injection position (FIG. 1) to a post injection position (FIG. 6).

FIG. 3 depicts the position of the elements in a relaxed, pre-injection state where the cover 50 is spaced from the user, U. in FIG. 3, first stage contact is made with the user, U. The cover 50 is forced backwardly toward terminal end. 52, the springs 48 are compressed and the needle tip penetrates the foam cap 54 through to the skin of the user, U. in order to administer the medicament, the body formed by members 12 and 14 is urged forward to the position shown in FIG. 5. This movement results in the pivotal movement of coupling 32 by the motion. of drive member 26. The coupling member 32 movement, in turn, by the pivotal connection, urges plunger 38 forward to discharge the medicament contained within barrel 40.

As will be realized from a review of FIGS. 4 and 5, once injection has been completed, indicator 28 extends rearwardly within the body to be visible within opening 16. This is indicative that the unit is used.

FIG. 6 illustrates the disposition of the components subsequent to an injection.

Figure 7:
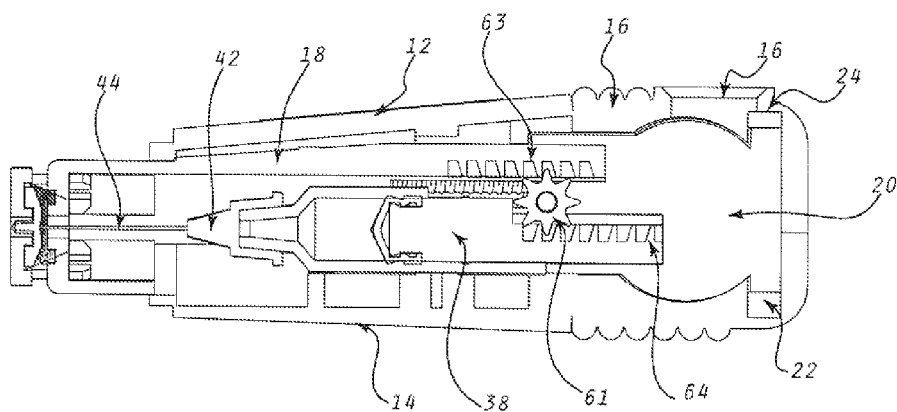
FIG. 7 is a cross section of an alternate embodiment.

Turning now to FIG. 7, shown is a longitudinal cross section of an alternate embodiment of the device, in this embodiment, the drive member is a toothed pinion 61, rotatably mounted to mount 20. Cooperating with pinion 61 is a pair of opposed toothed racks 63 and 64. Pinion 61 is received by racks 63 and 64 in the same manner as a rack and pinion system used in an abundance of mechanical systems. In the embodiment shown, rack 63 is integral with body member 18, while rack 64 is integral with plunger 38. Relative movement between the first body member and the second is the same as that discussed supra with respect to the first embodiment. As is evinced in the Figure, rack 63 is disposed in advance of rack 64. This staggered relationship allows for free movement of the outer body (members 12 and 14) to advance plunger 38.

Figure 8:
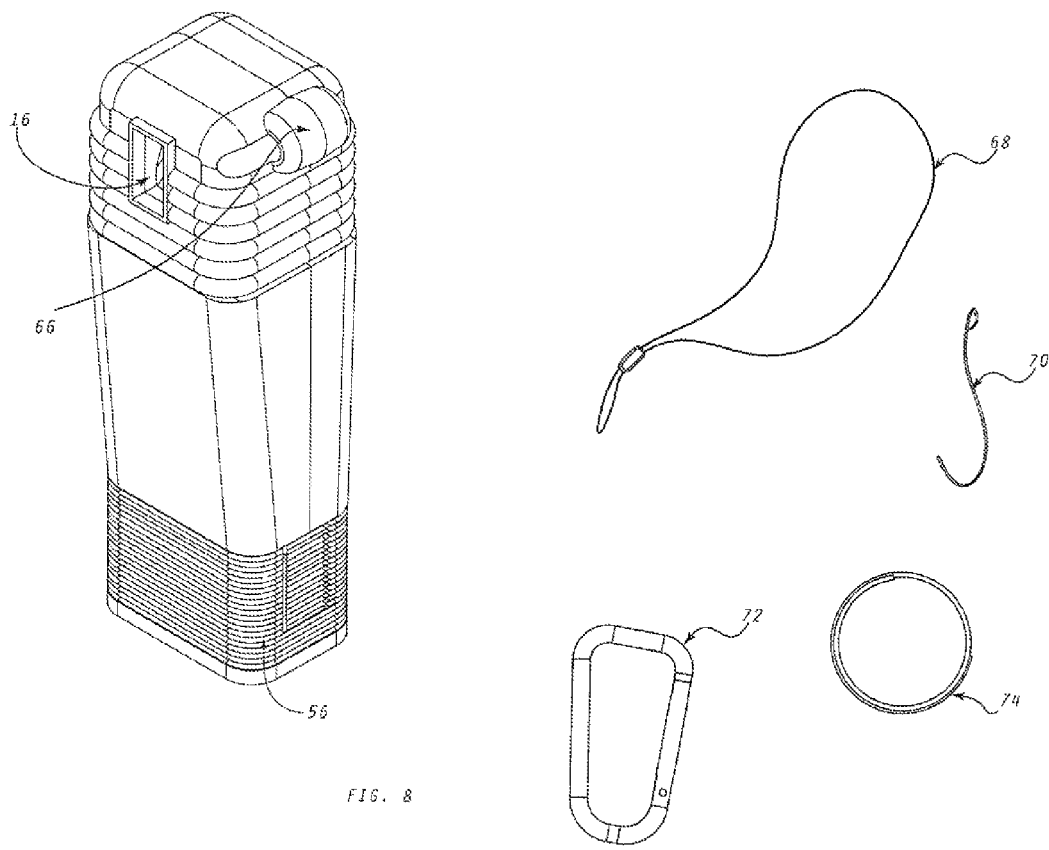
FIG. 8 is a perspective view of yet another embodiment.

FIG. 8 illustrates an embodiment of the device where an aperture 66 within the body is adapted to receive an elongate length 68, such as a lanyard, a hook 70, a clasp 72, a ring 74, etc. to allow for easier portability.

Figure 9:
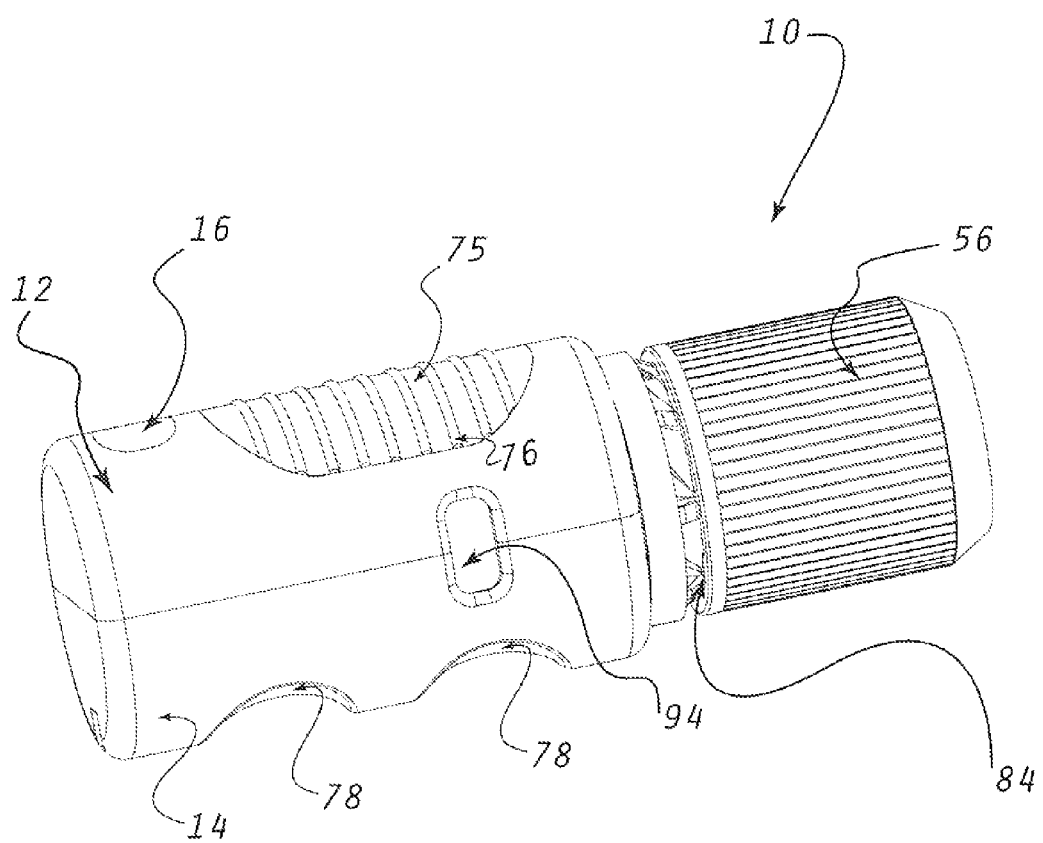
FIG. 9 is a perspective view of a further alternate embodiment of the present invention.

Referring now to FIG. 9, shown is a further embodiment of the present invention in an assembled state. The embodiment shown is generally similar to the embodiment that has been previously discussed, with this arrangement further including a top grip member 75 which, in the example, comprises a rubber material with a plurality of raised sections 76, which raised section 76 are in spaced relation to provide, for example, a thumb rest for actuating the device.

The material of which the top grip 74 may be made can include any material suitable for this purpose and may simply comprise the material of which the body members 12 and 14 are composed. In order to complement the use of the article, body 14 includes concavities 78, which concavities are useful to assist a user (not shown) in holding the device 10.

Figure 10:
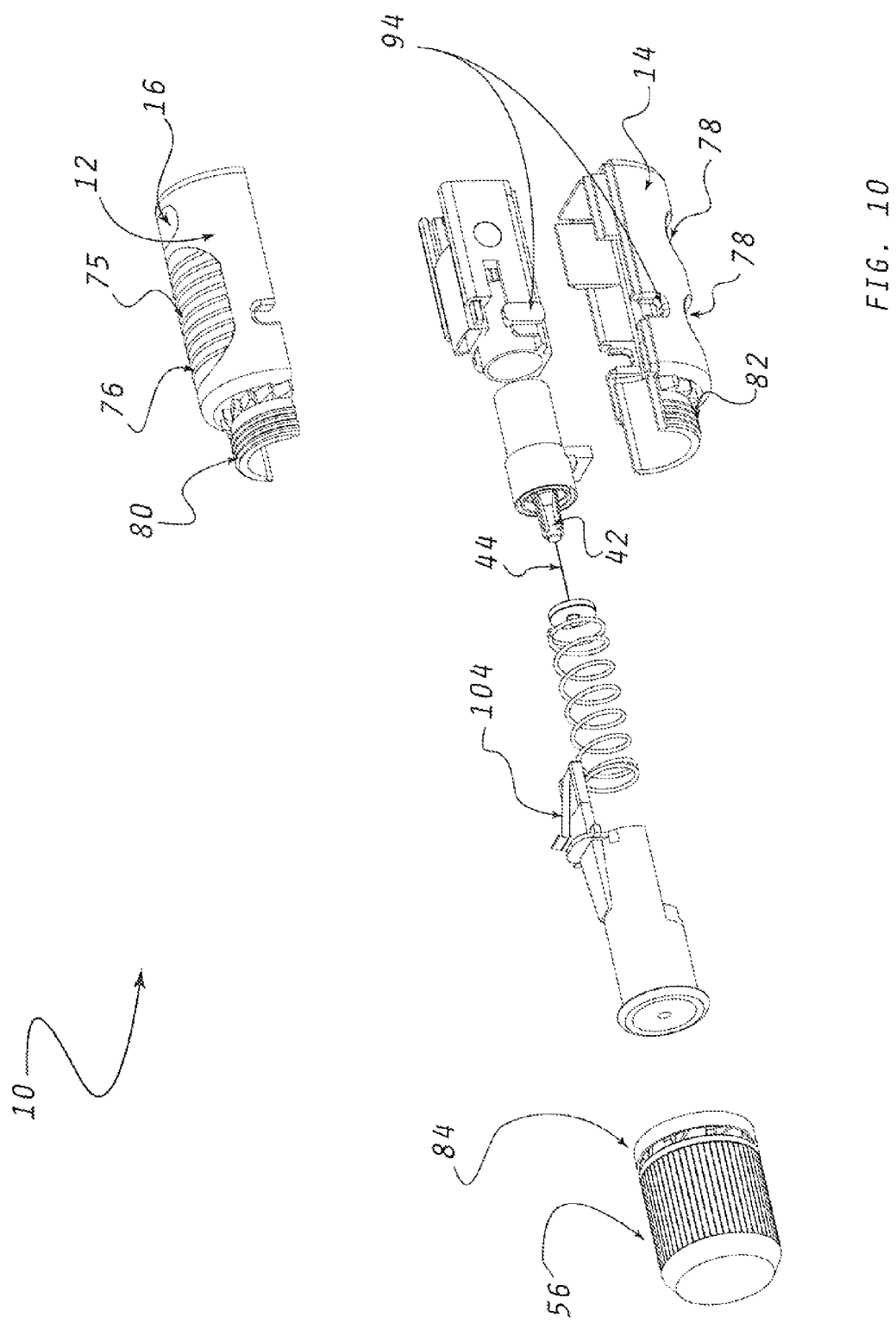
FIG. 10 is an exploded view of the device shown in FIG. 9.

Turning to FIG. 10, shown is an exploded view of the device shown generally in FIG. 9. Reference will be made to FIGS. 10 through 13 for the following description.

In this embodiment, each of the body members 12 and 14 includes a threaded section 80 and 82, respectively. This is for the purpose of engaging cap 56 which, in this embodiment, is threaded (not Shown) for purposes of engaging the threads 80 and 82. The cap 56 is of the variety that it is removable for a single use only. Such caps are known in the art. As a further security feature, the cap 56 may include a breakaway seal 84 which typically takes the form of a ring attached to the body of the cap 56 by disengageable or breakaway connectors as is well known in the art.

As has been indicated previously, body members 12 and 14 are referred to collectively as a first body member, whereas the second body member 18, in this embodiment, includes a needle cover 88, which needle cover 88 substantially surrounds the entire needle and tip. At the terminal end of the needle 44 there is provided the foam cap 54 which accommodates the tip of the needle 44 which also cooperates with a cover member 88 to effectively surround and close the needle 44. This is obviously contributory to the hygiene and sterility of the device. Disposed coaxially about needle 44 and within the internal volume of cover there is disposed a spring 90 which is positioned between the needle cover 88 of member 86 and seating 92 within second body member 18 as shown. This retains the spring 90 until the device 10 is intended for use.

As is evident from FIGS. 10 through 13, the first body member formed by body members 12 and 14 and the second body member 18 house the major components of the device and specifically, the plunger 38, barrel 40 needle hilt 42 and needle 44. As with the previous embodiments, second body member 18 includes the toothed rack coupling means 62, whereas the plunger 38 and more particularly, the arm of the plunger includes the second toothed rack coupling means 64. As with the previous embodiments, pinion 61 acts as a drive member which connects both of the racks 62 and 64. In this embodiment, observation window 94 is provided in the structure and visible through connected body members 12 and 14 to allow the user to determine whether barrel 40 contains any medicament and whether the medicament has been compromised.

Figure 11:
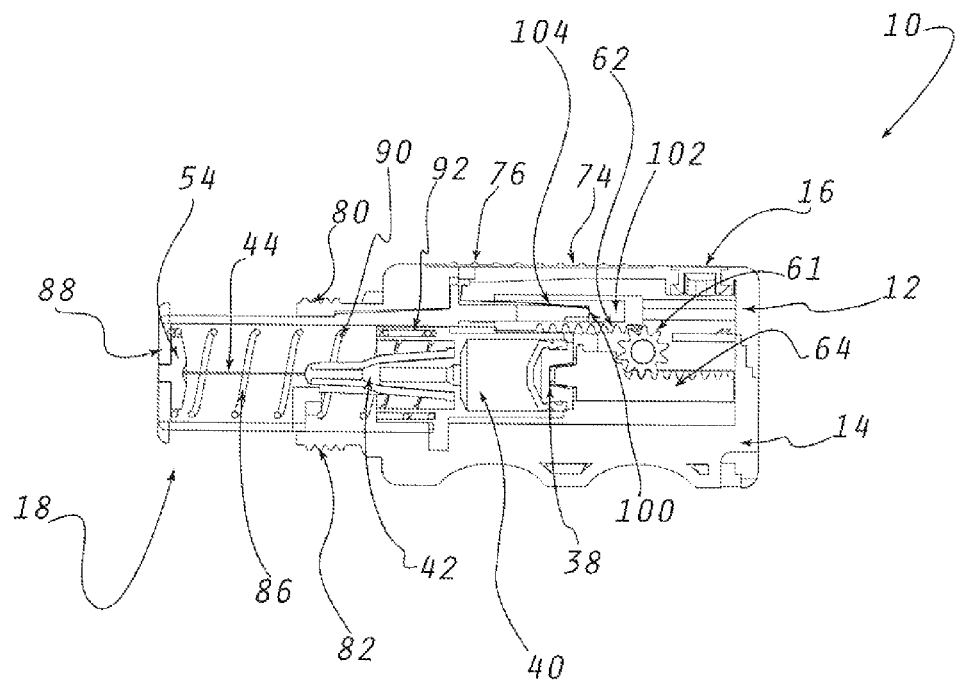
FIG. 11 is a longitudinal cross section of the device before use.

In the embodiment shown in FIGS. 9 through 13, body members 12, 14 and second body member 18 are coaxially mounted and designed for reciprocal movement. As a particularly beneficial advantage, in the embodiment shown in FIGS. 9 through 13 second body member 18, in opposition to the front cap 88, includes a terminal wall 100, As best seen in FIG. 11, terminal wail 100 is spaced from wall 102, which is formed by the connection of body members 12 and 14. This space permits movement of the body member 18 relative to assembled members 12 and 14 sufficiently to allow the needle 44 to penetrate cover 88 before injection. This avoids spillage and allows accurate injection of the medicament without wastage and allows for intramuscular injections.

Figure 13:
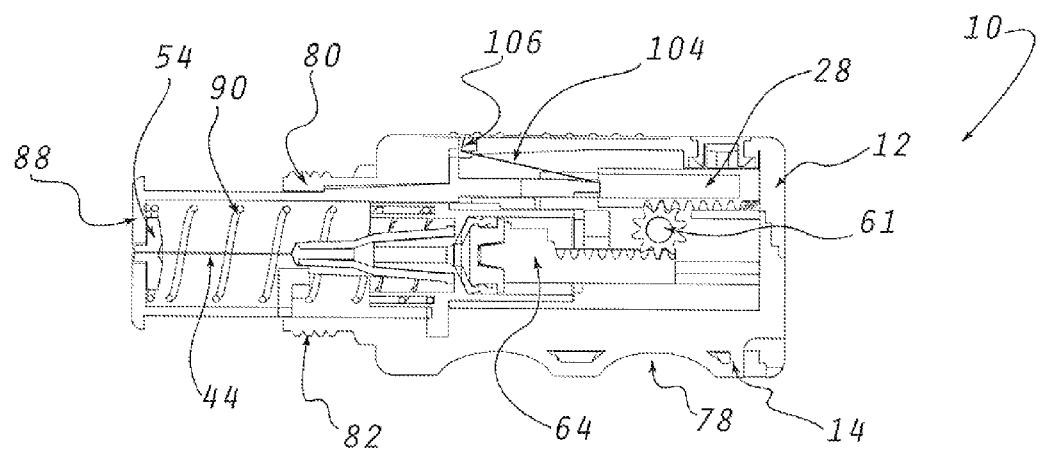
FIG. 13 is a longitudinal cross section of the device in a post use position.

As a further attendant advantage, the embodiment under discussion also provides for a locking mechanism 104, shown in the example as a leaf spring and best shown in FIGS. 10 and 13. Spring 104, when the device is in a ready to use position is compressed by disposition of body members 12, 14 and 18 as illustrated in FIG. 11.

Figure 12:
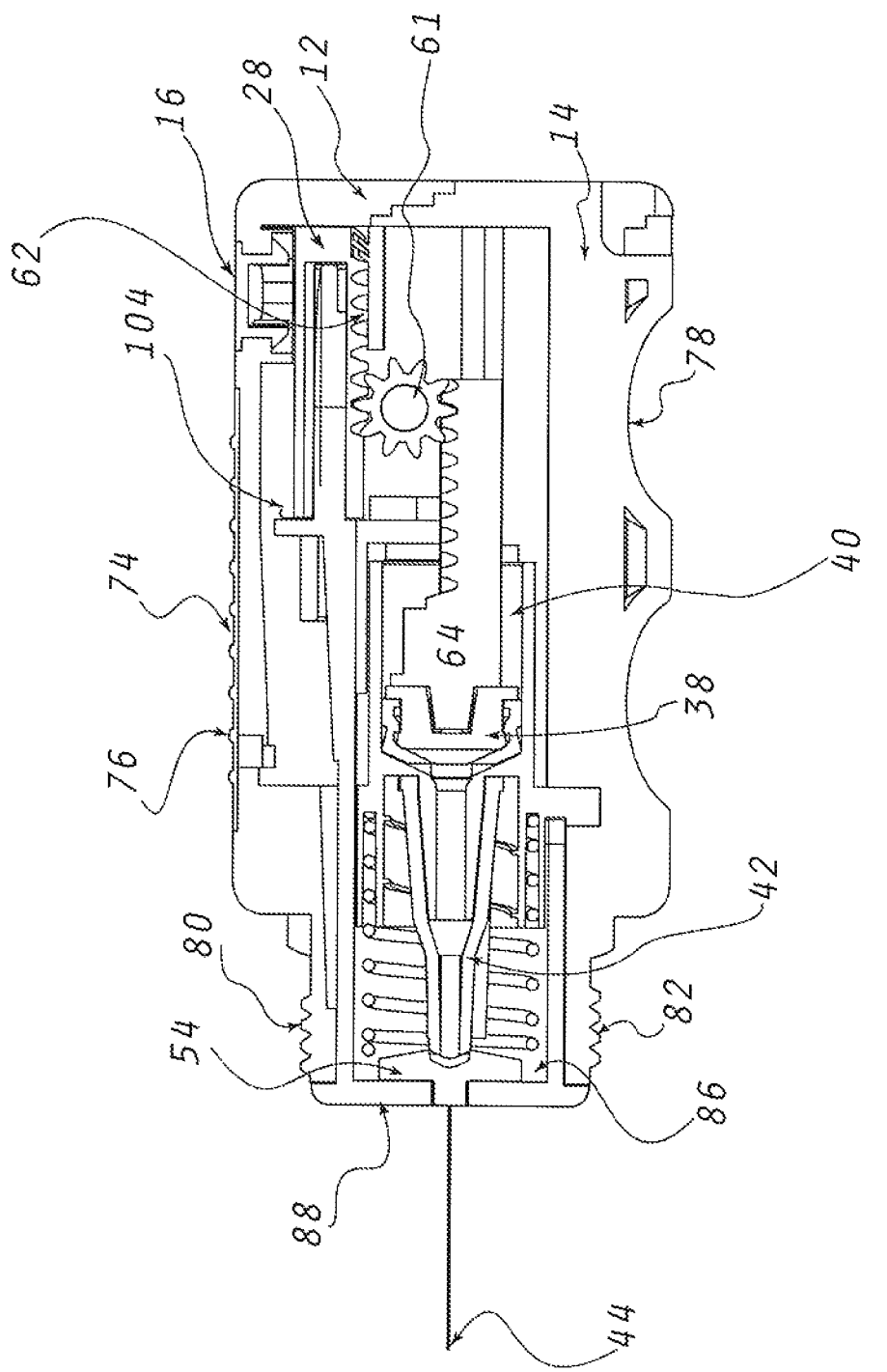
FIG. 12 is a longitudinal cross section of the device in a use position.

Turning to FIG. 12, the device 10 is shown in an injection position where the needle 44 has penetrated the foam cap 54 and end cap 88 and where second body member 18 is retracted within the first body member composed of members 12 and 14. As is evident, the spring 90 is compressed, with the plunger 38 moved forwardly within the barrel 40 and with the rack 64 moved forwardly relative to the position showing FIG. 11. In a similar manner, rack 63 is moved rearwardly as shown in FIG. 12. The locking member 104, is now compressed inside the gear rack 63 as shown in FIG. 12.

Turning now to FIG. 13, shown is a longitudinal cross-section of the device 10 subsequent to injection of the medicament. As is obvious from the illustration, once body member 18 is returned to the extended position with spring 90 relaxed, lock member 104 has nothing further to maintain a compressed state and therefore springs upwardly in a diagonal pattern as shown in FIG. 13, with the terminal end of 106 of spring 104 engaging the under surface of body member 14. This arrangement effectively locks retractable movement of body member 18 into the first body member 12, 14 whereby the device 10 cannot be reused. his is simply prevented by the lock arrangement 104. Further, as illustrated in FIG. 13, the second body member 18 fully extends to provide the cap 54 and end cap 88 to completely encapsulate and extend over the tip of needle 44 so that there is no possibility of inadvertent contact of the used needle with a user. As further benefit, as noted above with respect to the previous embodiments the opening 16 in body member 12 allows the user to determine whether the device has been discharged. A similar structure w that noted herein previously is provided for this benefit.

Figure 14:
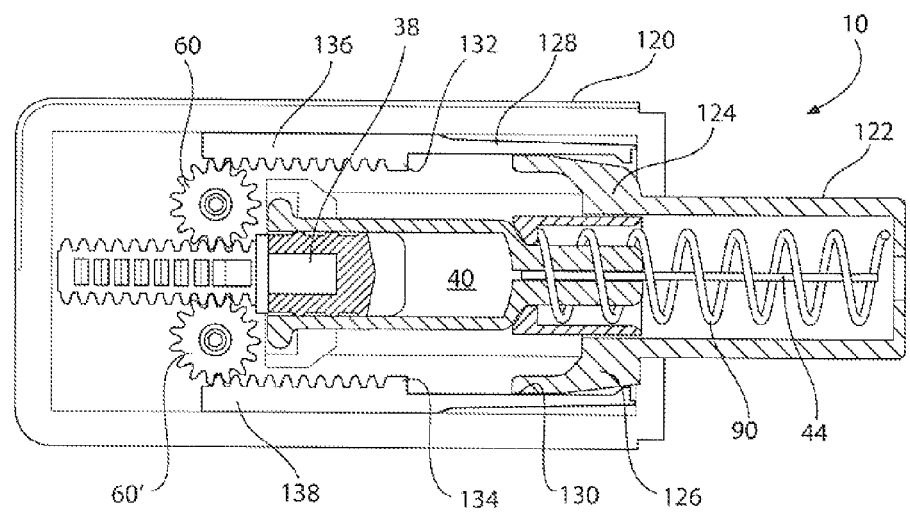
FIG. 14 is a longitudinal cross section of yet another embodiment of the present invention before use.

Referring now to FIG. 14, shown is a longitudinal cross section of a further embodiment according to the present invention. As noted herein previously similar numerals will be representative of previously discussed components. In this embodiment, there is an outside first body member 120 which cooperates with a second body member 122 which is coaxially mounted within body member 120 for reciprocal movement. Body member 122 houses the spring 90 and needle 44 in a protective manner as is shown in the Figure, i.e. the needle 44 is not exposed. At a distal point from the front of member 122 are abutting legs 124 and 126, each of which includes a terminal end portion 128 and 130, respectively.

Figure 15:
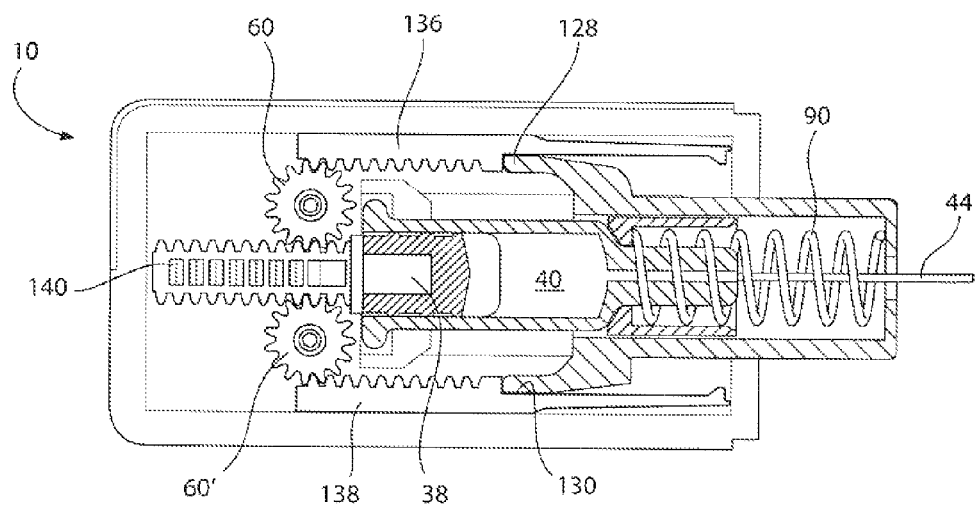
FIG. 15 is a view similar to FIG. 14 illustrating the position of the components at a second stage.

In use, once member 122 is urged rearwardly in a direction within body member 120, the needle 44 is at least partially exposed and the spring 90 is at least partially compressed as is evident from FIG. 15. Each of the terminal end portions 128 and 130, when in the position shown in FIG. 15, subsequently engages in corresponding abutments 132 and 134, respectively associated with a first rack 136 and a second rack 138 mounted within body member 120 for slidable movement therein. In this manner, corresponding abutments 132 and 134 effectively act as stops for terminal portions 128 and 130 of member 122.

As is generally common with earlier discussed embodiments, the device in this embodiment employs a rack and pinion drive mechanism. As such, rack 136 and 138 each individually engage pinion 61 and 60' as shown in the Figure.

Figure 16:
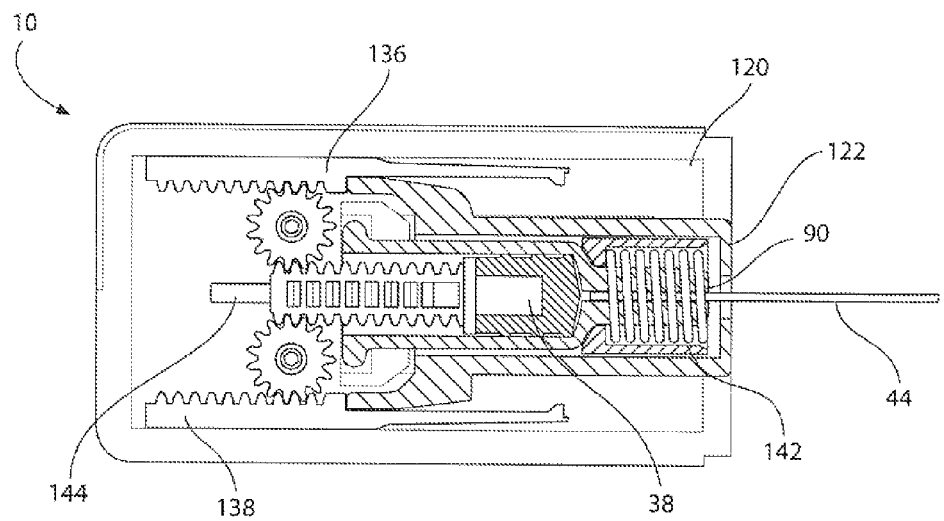
FIG. 16 is a view of the device in a fully retracted position in use.
Figure 18:
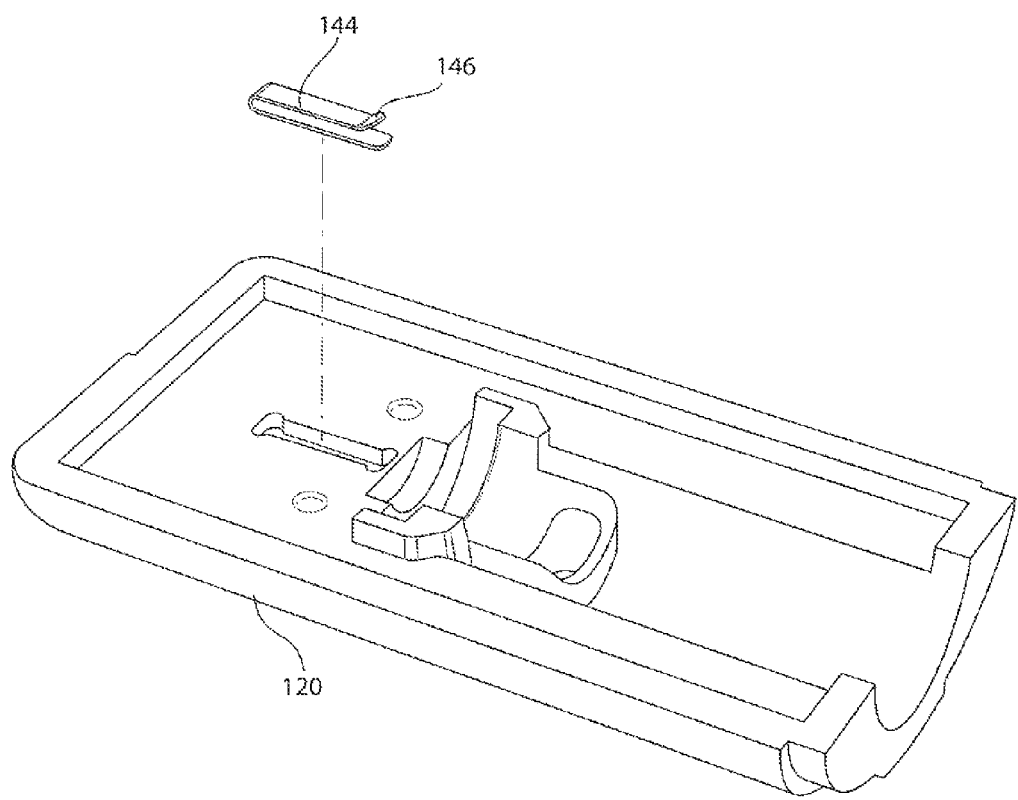
FIG. 18 is a view of the device with components removed to illustrate a spring member.

Since the abutments 132, 134 are engaged with respective terminal end portions 128 and 130 of member 122, the result is that further movement of member 122 results in the rotation of each of pinions 60 and 60' to the position shown in FIG. 16. As is generally similar to the previous embodiments, plunger 38 is movable within barrel 40 as is typically associated with syringe arrangements. The plunger 38, in this embodiment, has a rack 140 which engages each of pinions 60 and 60'. The result of this mechanical union is that upon further movement of body member 122 to the position shown in FIG. 16, i.e. within body member 120, the result is that the needle 44 is fully exposed with spring 90 fully compressed and plunger 38 in the full forward position for the discharge of the medicament into a user (not shown). In this position, the spring 90 is fully compressed and is retained with a retainer 142 coaxially positioned within body member 122. In this position, plunger 38 is locked into the position shown in FIG. 16 with a lock member 144 which is housed within body member 120 rearwardly of the plunger 38. In the embodiment shown, the lock member 144 comprises a leaf spring. The disposition of which is shown best in FIG. 18. The lock member or leaf spring 144 includes a lip 146 which abuts the rear portion of plunger 38 when in the position of FIG. 16 to prevent further use of the device 10 once the medicament has been discharged into a user (not shown). In this manner, lock member 144 remains in a standby position when the components within body member 120 are disposed in the positions shown in FIGS. 15 and 16.

Figure 17:
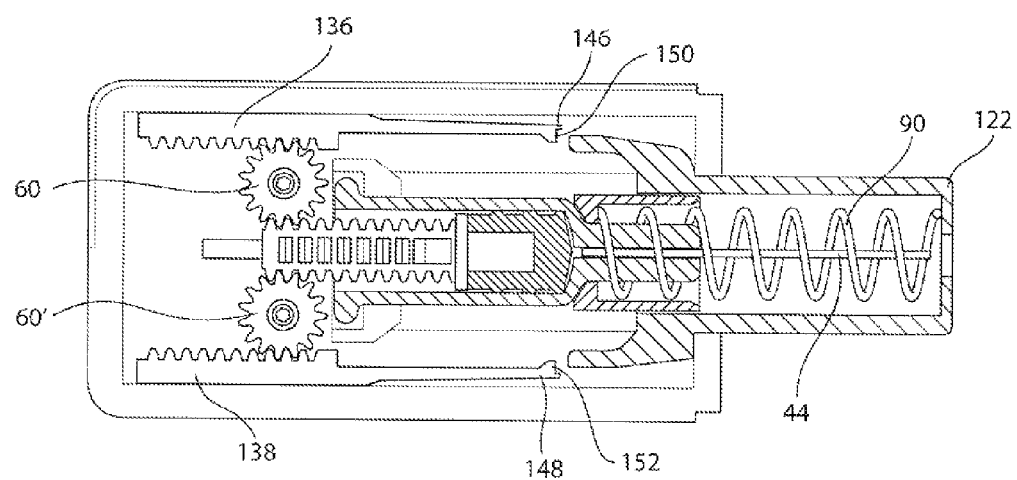
FIG. 17 is a view of the device subsequent to use.

Once locked, the compression force of spring 90 is released so that the spring 90 is a relaxed state as shown in FIG. 17. The force that is dissipated from spring 90 then urges body member 122 into a position where it completely surrounds and encapsulates needle 44 as shown in FIG. 17. As a particular convenient feature, each rack 136 and 138 includes at respective end portion 146 and 148 lock abutments 150 and 152, respectively. The lock abutments 150, 152 are used to prevent the inadvertent movement of body member 122 back within body member 120 in a reciprocating manner. This prevents entirely the inadvertent exposure of needle 44 so that is becomes impossible for the device 10 to be reused. Alternatively, the automatic injection device may comprise said first lock which comprises a detent at a terminal end of each extension.

Although the embodiments of the invention have been described above, it is limited thereto and it will be apparent to those skilled in the art that numerous modifications from part of the present invention insofar as they do not depart from the spirit, nature and scope of the described invention.

I claim:

1. An automatic injection device for dispensing a medicament, said device having a needle connected to a barrel adapted to retain medicament and a plunger within said barrel wherein said device comprises:
   an outside first body member and a second body member coaxially mounted for reciprocal movement within said outside first body member, said outside body member housing said needle, said barrel and said plunger;
   a first rack and a second rack housed within said outside first body member;
   a third rack connected to said plunger; and
   a pinion mounted within said outside first body member and between said first rack and said third rack and between said second rack and said third rack, said second body member including a needle cover biased to cover said needle and movable to expose said needle in use and to move said first rack and said second rack for urging said plunger into said barrel to dispense said medicament.

2. The automatic injection device as set forth in claim 1, wherein said first rack and said second rack each include an abutment for abutting legs connected to said needle cover.

3. The automatic injection device as set forth in claim 1, wherein said needle cover is biased with a spring.

4. The automatic injection device as set forth in claim 3, wherein said device includes a spring retainer positioned about said barrel and coaxial with said needle cover.

5. The automatic injection device as set forth in claim 2, wherein said device includes a first lock for preventing movement of said needle cover once biased to cover said needle subsequent to use.

6. The automatic injection device as set forth in claim 2, wherein said device includes a second lock for preventing movement of said plunger once positioned within said barrel.

7. The automatic injection device as set forth in claim 5, wherein said first lock is positioned on each of said first rack and said second rack.

8. The automatic injection device as set forth in claim 7, wherein said first lock is positioned at a point distal from a rack portion of each of said first rack and said second rack.

9. The automatic injection device as set forth in claim 8, wherein said first lock is positioned on a leg extension of each of said first rack and said second rack.

10. The automatic injection device as set forth in claim 9, wherein said first lock comprises a detent at a terminal end of each extension.

11. The automatic injection device as set forth in claim 6, wherein said second lock comprises a biasing member positioned on an inside surface of said outside body member.

12. The automatic injection device as set forth in claim 11, wherein said biasing member comprises a leaf spring.

13. The automatic injection device as set forth in claim 1, wherein said first rack and said second rack are mounted for sliding motion within said outside first body member.

14. The automatic injection device as set forth in claim 1, wherein said pinion is mounted for rotation within said outside first body member.

15. The automatic injection device as set forth in claim 1, wherein said device is a single use device.

16. The automatic injection device as set forth in claim 1, wherein said device includes a break away cap.

* * * * *